United States Patent
Hsi et al.

(10) Patent No.: US 11,300,550 B2
(45) Date of Patent: Apr. 12, 2022

(54) SYSTEM FOR INTEGRATING MULTIPLE CHEMICAL SENSOR DATA TO DETECT AN UNMEASURED COMPOUND

(71) Applicant: Honeywell International Inc., Morris Plains, NJ (US)

(72) Inventors: Peter Hsi, Dublin, CA (US); James Liu, Livermore, CA (US); Thomas Negre, San Jose, CA (US); Praveen Sharma, Dublin, CA (US)

(73) Assignee: Honeywell International Inc., Morris Plains, NJ (US)

( * ) Notice: Subject to any disclaimer, the term of this patent is extended or adjusted under 35 U.S.C. 154(b) by 485 days.

(21) Appl. No.: 15/564,163

(22) PCT Filed: Apr. 19, 2016

(86) PCT No.: PCT/US2016/028286
§ 371 (c)(1),
(2) Date: Oct. 3, 2017

(87) PCT Pub. No.: WO2016/176085
PCT Pub. Date: Nov. 3, 2016

(65) Prior Publication Data
US 2018/0080910 A1     Mar. 22, 2018

Related U.S. Application Data

(60) Provisional application No. 62/155,040, filed on Apr. 30, 2015.

(30) Foreign Application Priority Data

Apr. 29, 2015   (IN) ............................ 2186/CHE/2015

(51) Int. Cl.
*G01N 33/00*     (2006.01)

(52) U.S. Cl.
CPC ............................. *G01N 33/0031* (2013.01)

(58) Field of Classification Search
CPC ........... G01N 33/0031; G01N 33/0059; G01N 33/0065; G01N 33/0063; A41D 13/11; B01D 46/0091
See application file for complete search history.

(56) References Cited

U.S. PATENT DOCUMENTS 6,165,347 A  *  12/2000  Warburton ......... G01N 27/4045
                                                             204/409
6,631,333 B1     10/2003  Lewis et al.
(Continued)

FOREIGN PATENT DOCUMENTS

CN      101000318 A     7/2007
CN      201876447 U     6/2011
(Continued)

OTHER PUBLICATIONS

MSDSonline, From MSDS to SDS—GHS Brings Big Changes to Safety Data Sheets in HazCom 2012, Aug. 20, 2012 [retrieved on Jul. 27, 2020], Retrieved from the Internet:< URL: https://www.msdsonline.com/2012/08/20/from-msds-to-sds-ghs-brings-big-changes-to-safety-data-sheets-in-hazcom-2012/>. (Year: 2012).*

(Continued)

*Primary Examiner* — John E Breene
*Assistant Examiner* — Liam R Casey
(74) *Attorney, Agent, or Firm* — Alston & Bird LLP (57) ABSTRACT

Methods for determining the presence of an unmeasured chemical in an environment can include receiving a plurality of sensor readings from a plurality of chemical sensors, wherein each chemical sensor of the plurality of chemical sensors is configured to detect a different chemical, determining a cross-sensitivity pattern from one or more unmeasured chemicals in the plurality of sensor readings, compar- (Continued)

ing the cross-sensitivity pattern with one or more known chemical patterns, determining that the cross-sensitivity pattern matches at least one of the one or more known chemical patterns that correspond to one or more chemicals, and identifying one or more unmeasured chemicals based on determining that the cross-sensitivity pattern matches the at least one of the one or more known chemical patterns.

20 Claims, 2 Drawing Sheets

(56) References Cited

U.S. PATENT DOCUMENTS

| | | | |
|---|---|---|---|
| 7,019,652 | B2 | 3/2006 | Richardson |
| 7,460,958 | B2 | 12/2008 | Walsh et al. |
| 2001/0013026 | A1 | 8/2001 | Shaffer |
| 2003/0135971 | A1* | 7/2003 | Liberman .......... B01D 67/0041 29/419.1 |
| 2005/0227258 | A1* | 10/2005 | Bright .................. B01J 20/268 435/6.19 |
| 2005/0241935 | A1* | 11/2005 | Lewis .................. G01N 27/126 204/403.01 |
| 2006/0140425 | A1 | 6/2006 | Berg et al. |
| 2009/0058600 | A1* | 3/2009 | Krepel .................. G07C 11/00 340/10.1 |
| 2009/0085873 | A1 | 4/2009 | Betts et al. |
| 2010/0198521 | A1* | 8/2010 | Haick ................ G01N 27/4146 702/19 |
| 2011/0006894 | A1* | 1/2011 | Witwer ................. G06Q 10/06 340/539.11 |
| 2011/0063116 | A1 | 3/2011 | Lepley et al. |
| 2011/0227700 | A1* | 9/2011 | Hamerly ................ A62B 9/006 340/10.1 |
| 2012/0154578 | A1* | 6/2012 | Bzorgi .................. G08B 21/12 348/143 |
| 2012/0238471 | A1* | 9/2012 | Pinchuk .......... G01N 33/54373 506/12 |
| 2013/0150261 | A1 | 6/2013 | Haick et al. |
| 2013/0253898 | A1* | 9/2013 | Meagher ................ G06N 20/00 703/18 |
| 2013/0282609 | A1* | 10/2013 | Au .......................... F16P 3/142 705/325 |
| 2014/0201182 | A1* | 7/2014 | Amin .................. G06F 16/2455 707/706 |
| 2014/0377877 | A1* | 12/2014 | Burgi ................ G01N 33/4972 436/120 |
| 2018/0089976 | A1* | 3/2018 | Yarlagadda .... G06Q 10/063118 |

FOREIGN PATENT DOCUMENTS

| | | |
|---|---|---|
| CN | 103134850 A | 6/2013 |
| CN | 103308650 A | 9/2013 |
| CN | 103622685 A | 3/2014 |
| CN | 103973447 A | 8/2014 |
| CN | 104237456 A | 12/2014 |
| CN | 104306118 A | 1/2015 |
| CN | 107533041 A | 1/2018 |
| DE | 3519435 A1 | 12/1986 |
| EP | 3289349 A1 | 3/2018 |
| WO | 99/24216 A1 | 5/1999 |
| WO | 2016176085 A1 | 11/2016 |

OTHER PUBLICATIONS

CCOHS, Understanding an MSDS, Mar. 21, 2005 [retrieved on Jul. 27, 2020], Retrieved from the Internet: < URL: https://web.archive.org/web/20050321212832/https://www.ccohs.ca/products/Supplements/MSDS_FTSS/msds_understand.html>. (Year: 2005).*
United State Department of Labor, OSHA Brief: Hazard Communication Standard: Safety Data Sheets, Apr. 4, 2013 [retrieved on Jul. 27, 2020], Retrieved from the Internet:< URL: https://web.archive.org/web/20130404121255/https://www.osha.gov/Publications/OSHA3514.html>. (Year: 2013).*
U.S. Department of Health & Human Services, "Rescuer Safety—Personal Protective Equipment," Aug. 13, 2011 [retrieved on Jan. 13, 2021]. Retrieved from the Internet:< URL: https://web.archive.org/web/20110813123252/https://chemm.nlm.nih.gov/ppe.htm>. (Year: 2011).*
U.S. Environmental Protection Agency, "Personal Protective Equipment," Oct. 11, 2014 [retrieved on Jan. 13, 2021]. Retrieved from the Internet:< URL: https://web.archive.org/web/20141011012600/https://www.epa.gov/emergency-response/personal-protective-equipment>. (Year: 2014).*
International Application No. PCT/US2016/028286, International Search Report, dated Jul. 6, 2016, 4 pages.
International Application No. PCT/US2016/028286, Written Opinion of the International Searching Authority, dated Jul. 6, 2016, 6 pages.
Zhang Let et al: "Performance Study of Multilayer Perceptrons in a Low-Cost Electronic Nose", IEEE Transactions on Instrumentation and Measurement, IEEE Service Center, Piscataway, NJ, US, vol. 63, No. 7 Jul. 1, 2014, pp. 1670-1679.
International Application No. PCT/US2016/028286, International Preliminary Report on Patentability, dated Oct. 31, 2017, 7 pages.
Europe Patent Application No. 16720266.2, Communication pursuant to Rules 161(1) and 162 EPC, dated Dec. 6, 2017, 2 pages.
Annex to the communication dated Jan. 23, 2019 for EP Application No. 16720266.
Annex to the communication dated May 16, 2019 for EP Application No. 16720266.
Annex to the communication dated Nov. 7, 2019 for EP Application No. 16720266.
Annex to the communication dated Nov. 29, 2019 for EP Application No. 16720266.
CN Search report dated Nov. 24, 2019 for CN Application No. 201680024708.
Communication from the Examining Division dated Jan. 23, 2019 for EP Application No. 16720266.
English Translation of CN Office Action dated Dec. 2, 2019 for CN Application No. 201680024708.
English Translation of CN Office Action, including Supplemental Search Report, dated Jul. 27, 2020 for CN Application No. 201680024708.
European Intention to Grant received for EP Application No. 16720266.2, dated Dec. 18, 2019.
European Invitiation to File a Search Results or Statement of Non-Availability pursuant to Rule 70b(1) received for EP Application No. 16720266.2, dated Jul. 24, 2018.
European Minutes of Oral Proceeding before the Examining Division received for EP Application No. 16720266.2, dated Nov. 29, 2019.
European Summons to Attend Oral Hearing pursuant to Rule 115(1) EPC received for EP Application No. 16720266.2, May 16, 2019.
European Decision to Grant received for EP Application No. 16720266.2, dated May 8, 2020.
Extended European Search Report dated Jul. 20, 2020 for EP Application No. 20171757.6.
CN Office Action dated Oct. 29, 2020 for CN Application No. 201680024708.
English translation of CN Office Action dated Oct. 29, 2020 for CN Application No. 201680024708.
Intention to grant dated Jul. 2, 2021 for EP Application No. 20171757, 7 pages.
Decision to grant a European patent received for EP Application No. 20171757.6, dated Nov. 11, 2021, 2 pages.
CN Office Action, including Search Report, dated Jan. 17, 2022 for CN Application No. 202110339001, 9 pages.
English Translation of CN Office Action, including Search Report, dated Jan. 17, 2022 for CN Application No. 202110339001, 11 pages.

* cited by examiner

SYSTEM FOR INTEGRATING MULTIPLE CHEMICAL SENSOR DATA TO DETECT AN UNMEASURED COMPOUND

CROSS-REFERENCE TO RELATED APPLICATIONS

The present application claims priority to and is the National Stage of International Application No. PCT/US2016/028286 filed on Apr. 19, 2016 and entitled "System for Integrating Multiple Chemical Sensor Data to Detect an Unmeasured Compound" which claims priority to U.S. Provisional Patent Application Ser. No. 62/155,040 filed on Apr. 30, 2015 and entitled "System for Integrating Multiple Chemical Sensor Data to Detect an Unmeasured Compound." This application also claims priority to Indian Provisional Patent Application No. 2186/CHE/2015 filed on Apr. 29, 2015 with the Intellectual Property Office of India and entitled "System for Integrating Multiple Chemical Sensor Data to Detect an Unmeasured Compound," wherein International Application No. PCT/US2016/028286, U.S. Provisional Patent Application Ser. No. 62/155,040 and Indian Provisional Patent Application No. 2186/CHE/2015 are incorporated herein by reference in their entirety.

BACKGROUND

Various systems exist to allow for the detection of compounds in an environment. Various sensor designs exist, and these sensors can be used to detect the presence of a compound. However, in some industrial settings a large number of chemical compounds can be present. The detection of all of these compounds may require a large number of sensors across a relatively large area. Even if some compounds do not need to be monitored, they may interfere with sensors designed to monitor various compounds of interest. In some cases, misidentification of a measured value can result due to the interfering effects of a gas that is not being directly measured, which can lead to false alarms within a facility. The resulting system to monitor a region can be complex, expensive, and prone to misidentifications and false alarms.

SUMMARY

In an embodiment, a method of determining the presence of an unmeasured chemical in an environment can include receiving a plurality of sensor readings from a plurality of chemical sensors, wherein each chemical sensor of the plurality of chemical sensors is configured to detect a different chemical, determining a cross-sensitivity pattern from one or more unmeasured chemicals in the plurality of sensor readings, comparing the cross-sensitivity pattern with one or more known chemical patterns, determining that the cross-sensitivity pattern matches at least one of the one or more known chemical patterns that correspond to one or more chemicals, and identifying one or more unmeasured chemicals based on determining that the cross-sensitivity pattern matches the at least one of the one or more known chemical patterns.

In an embodiment, a chemical compound measurement system comprises a memory storing an exposure application, a pattern store storing known chemical patterns, and a processor. The exposure application, when executed on the processor, configures the processor to: receive a plurality of sensor readings from a plurality of chemical sensors, where each chemical sensor of the plurality of chemical sensors is configured to detect a different chemical, determine a cross-sensitivity pattern from one or more unmeasured chemicals in the plurality of sensor readings, compare the cross-sensitivity pattern with one or more of the known chemical patterns, determining that the cross-sensitivity pattern matches at least one of the one or more known chemical patterns, where the one or more known chemical patterns correspond to one or more chemicals, and identifying one or more unmeasured chemicals based on determining that the cross-sensitivity pattern matches the at least one of the one or more known chemical patterns.

In an embodiment, a method of determining the presence of a compound in an environment comprises receiving a plurality of sensor outputs from a plurality of chemical sensors, determining a cross-sensitivity pattern resulting from the presence of the unmeasured compound using the plurality of sensor outputs, comparing the cross-sensitivity pattern with one or more known chemical patterns, determining that the cross-sensitivity pattern matches at least one of the one or more known chemical patterns, wherein the one or more known chemical patterns correspond to one or more compounds, and identifying the unmeasured compound based on determining that the cross-sensitivity pattern matches the at least one of the one or more known chemical patterns. Each chemical sensor of the plurality of chemical sensors is configured to detect a different chemical, and a ratio of a first portion of each of the sensor outputs resulting from a detected compound to a second portion of the sensor output resulting from an unmeasured compound is at least about 2:1.

Embodiments described herein comprise a combination of features and characteristics intended to address various shortcomings associated with certain prior devices, systems, and methods. The foregoing has outlined rather broadly the features and technical characteristics of the disclosed embodiments in order that the detailed description that follows may be better understood. The various characteristics and features described above, as well as others, will be readily apparent to those skilled in the art upon reading the following detailed description, and by referring to the accompanying drawings. It should be appreciated that the conception and the specific embodiments disclosed may be readily utilized as a basis for modifying or designing other structures for carrying out the same purposes as the disclosed embodiments. It should also be realized that such equivalent constructions do not depart from the spirit and scope of the principles disclosed herein.

BRIEF DESCRIPTION OF THE DRAWINGS

For a more complete understanding of the present disclosure and the advantages thereof, reference is now made to the following brief description, taken in connection with the accompanying drawings and detailed description, wherein like reference numerals represent like parts.

DETAILED DESCRIPTION

It should be understood at the outset that although illustrative implementations of one or more embodiments are illustrated below, the disclosed devices, systems and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents.

In an embodiment, a workplace safety system may allow a plurality of sensors associated with environmental, location, movement, and biometric information to be used to provide an integrated safety solution for one or more workers. A number of sensors can be employed, and the data from the sensors can be combined to provide a better view of the personal safety of the workers. For example, data from fixed and/or mobile sensors can be used to detect chemical components of an environment, environmental conditions (e.g., temperature, pressure, wind speed, wind direction, etc.), vibration levels, noise levels, biometric parameters (e.g., heart rate, body temperature, respiration rate, etc.), location (e.g., including 2-dimensional and/or 3-dimensional position), and the like. The resulting data can be relayed through a communication module to a server, where the data can be combined to provide an overall view of a workers risk factor. Various information such as alarms, notifications, information (e.g., maintenance protocols, instructions, live help, etc.), and the like can be relayed back to the worker through the system. The system may provide for better personal safety as a result of real time or near real time updates, improved productivity through the processing of multiple types of data, and better worker compliance with safety protocols by providing real time or near real time monitoring of personal protective equipment use, qualifications, and training for a variety of activities. All of these systems provide feedback to the worker to improve productivity, compliance, and safety in ways that have not previously been as efficient.

In a first example, a plurality of chemical sensors can be used to detect a plurality of compounds in an environment. The resulting measurements can be used to identify a cross-sensitivity (e.g., an interference caused in the measurement of a desired chemical by a different chemical present in the environment being detected by the sensor) from one or more of the sensors and matched to a set of patterns. The resulting pattern matching process can be used to identify a chemical in the environment that is not directly measured. The specific cross-sensitivity for each type of chemical sensor may provide for representative patterns that are specific to an unmeasured compound. In this way, the cross-sensitivity of a given chemical component for a given set of chemical sensors can be thought of as having a fingerprint that can be matched to a database of chemical fingerprints to identify the compound. The resulting identification of the unmeasured compound may provide not only an identification of the chemical, but also a measure of the chemical concentration in the ambient atmosphere. The resulting identification of the chemical and its concentration can be used to eliminate the cross-sensitivity from the measured compounds. The determined concentration can also be compared to an exposure threshold to provide a level of safety with respect to the chemical, even when a sensor is not present that directly detects the chemical. This may extend the detection range of a multi-sensor array as well as reducing the need for specialty chemical sensors in certain situations.

A feedback and learning mechanism can be used to indicate the presence of the chemical and its fingerprint among other chemicals. This may provide an updated database of chemical fingerprints for use in different environments. The fingerprints or patterns can be distributed to a multi-sensor array to allow for real time or near real time sensing of the detected chemicals as well as the undetected chemicals. Further, the correlation between sensor arrays in a facility may provide for improved detection and mapping of each chemical within the facility. This system may use multiple sensor inputs to provide an indication of unmeasured components to improve the safety of workers in a facility.

The determined chemical identity and concentrations can be used, alone or in combination with other determined and/or measured compounds to create a mapping of the chemical concentrations in a facility. The mapping of a facility can be performed when sufficient spatial information is available, and a worker can proactively be warned not to enter certain areas based on the combined effects of the exposure to chemicals. The type of equipment used by the worker can be taken into account in this analysis. In some embodiments, the system may suggest the appropriate equipment, which may be more than the standard safety equipment. This personal recommendation may increase the workers productivity by avoiding having the worker return to a safety area to exchange their equipment during the performance of a job.

Figure 1:
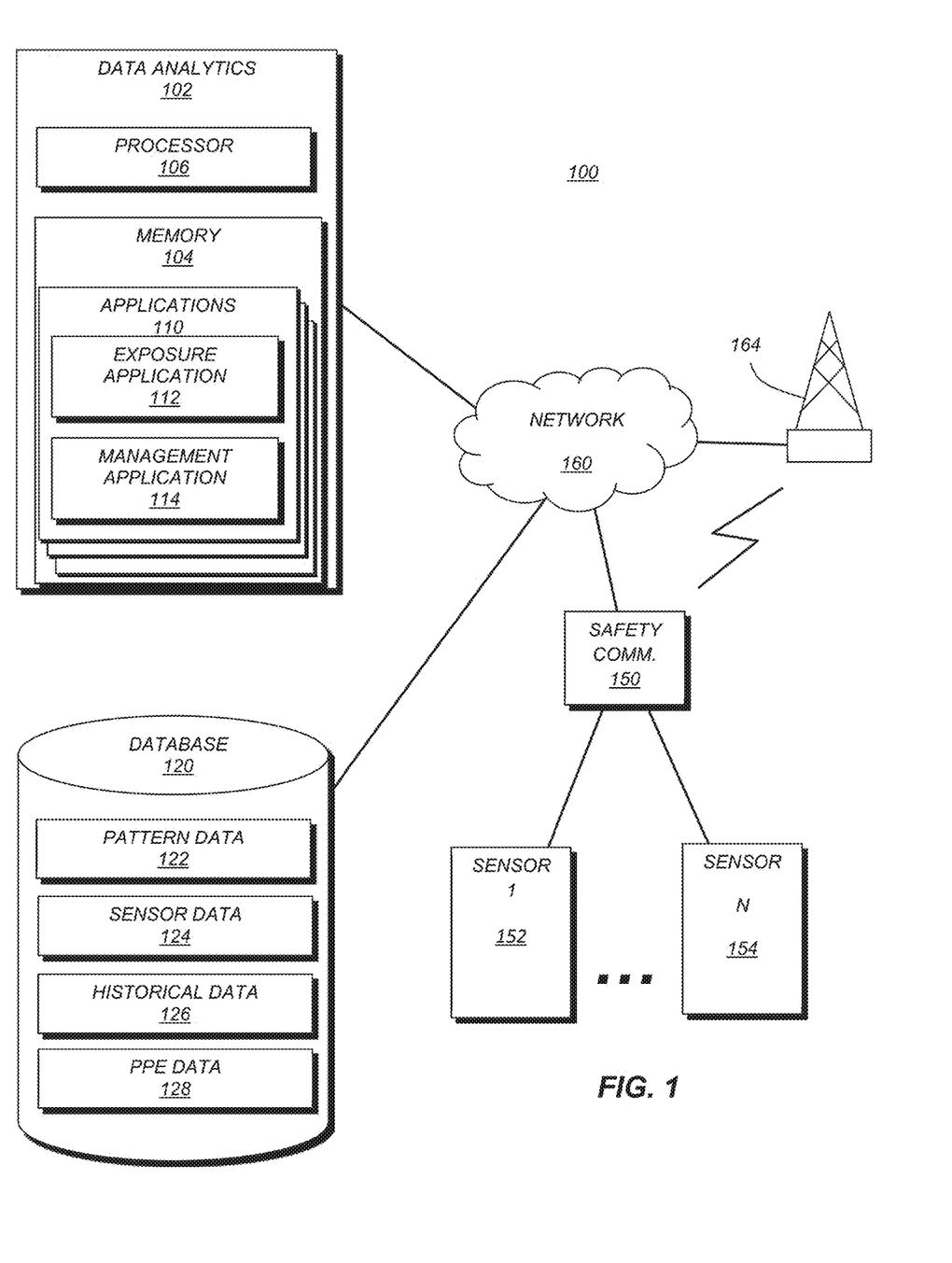
FIG. 1 schematically illustrates a sensor system for detecting one or more chemical compounds in an environment according to an embodiment disclosed herein.

Referring to FIG. 1, a system 100 for providing workplace safety based on a combination of sensor inputs is illustrated. As shown in FIG. 1, the system may comprise a plurality of sensors 152, 154 in signal communication with a communication node such as a safety communicator 150. The safety communicator 150 may provide a data connection to a data analytics server 102 and/or a database 120 through a network 160. The safety communicator 150 may be wirelessly coupled to the network through an access point such as a wireless fidelity (Wi-Fi), Bluetooth, or cellular connection (e.g., through a wireless service tower 164). In some embodiments, the sensors can be in signal communication with a wired communication node such as a router or other device that can communicate with the data analytics server 102 and/or a database 120 through a network 160.

In the system 100, the network 160 may be the internet representing a worldwide collection of networks and gateways that use the Transmission Control Protocol/Internet Protocol (TCP/IP) suite of protocols to communicate with one another. In some embodiments, the system 100 may also be implemented as a number of different types of networks such as, for example, an intranet, a local area network (LAN), or a wide area network (WAN). FIG. 1 is intended as an example and not as an architectural limitation for varying embodiments.

The data analytics server 102 can comprise a memory 104, a processor 106, and one or more applications 110 stored in the memory that can configure the processor 106 to perform certain functions. In general, the data analytics server 102 is configured to receive sensor data such as indications of ambient chemical concentrations (e.g., current levels, voltage levels, calculated concentrations, etc.), biometric data, environmental data, and/or location data associated with a worker and/or one or more sensors and process the data to provide information to the worker and/or decision makers at a facility. The data analytics server 102 is in communication with a database 120 that serves to store information used within the system 100. The database 120 can include a chemical pattern data store 122, a sensor calibration data store 124, a historical data store 126 and/or a personal protective equipment (PPE) data store 128.

The applications 110 can include an exposure application 112 and/or a management application 114. Each application can communicate with one or more of the sensors 152, 154 and/or the safety communicator 150. The exposure application 112 can receive the sensor data and perform pattern matching based on the plurality of chemical sensor measurements. The resulting analysis can be used to detect one or more unmeasured chemicals within a location (e.g., within one or more areas of a facility) and provide information to the safety communicator 150 and/or one or more sensors 152, 154. For example, the information can include alerts, notifications, information for performing a procedure, inputs (e.g., triggers, etc.) to safety devices, or the like.

In an embodiment, the exposure application 112 can receive a plurality of inputs from the sensors. As described in more detail below, the sensors can measure ambient chemical concentrations, location information, environmental information, biometric information from one or more individuals, noise levels, and the like. The sensor data can be stored in the historical data store 126 and used with the system. The exposure application 112 can use the sensor data along with the location data for the sensors to develop an exposure mapping of a facility for both the detected chemicals and the one or more chemicals determined to be present based on the multiple sensor inputs. For example, a model can be used to predict the exposure at one or more locations within the facility, and the prediction can include areas where sensors are not present. The exposure values can be determined for various environmental hazards including chemical exposure, noise exposure, light and heat exposure and the like.

Once the exposure application 112 has determined exposure levels within a facility, the exposure values for a number of environmental hazards can be combined to provide a better view of the personal safety of the workers. For example, data for a chemical exposure at a given location can be used to determine and predict a potential chemical exposure at that location. The sensor data can be stored in the sensor data store 124 and accessed by the exposure application 112 along with the pattern data 122 as part of the determination of when one or more unmeasured chemicals are present. The resulting measured sensor data and determined chemical data can be stored in the historical data store 126. In some embodiments, the determination of the presence of an unmeasured chemical can be performed on the safety communicator rather than a back-end server such as data analytics server 102.

The measurement and determination process can be repeated periodically by the exposure application 112. For example, the exposure application may update the exposure values at an interval of less than one minute, less than five minutes, less than thirty minutes, or less than an hour. The rate at which the exposure values and/or the risk value rating are updated may be based, at least in part, on the rate at which the sensor data (e.g., sensor values, location data, etc.) is updated and communicated back to the data analytics server 102.

In some embodiments, the exposure application 112 may monitor the exposure value with respect to the location of one or more individuals and provide feedback to a manager and/or the individuals based on the exposure value associated with the individual's location and/or expected location based on predicted movements. The exposure value can be determined based on a base case for an individual without any PPE, or in some embodiments, an individual's PPE selection can be included in the determination of the exposure value. Using the plurality of sensor readings (with or without the PPE considerations) to arrive at the exposure value may allow a worker's current exposure to be evaluated and communicated to each worker.

When a worker is at a location at which the exposure value exceeds a threshold, an alert, an alarm, a notification, and/or information (e.g., maintenance protocols, instructions, live help, etc.), and the like can be relayed back to the worker through the system. For example, the data analytics server 102 may send a message to the safety communicator 150 to display the information. The alerts can indicate the level of exposure, a notification that additional PPE is required, or an indication that the individual should not enter a specified area or leave an area if the individuals are already within the area. The ability to update the data and determine the exposure value in real time or near real time may provide for better personal safety as a result of real time or near real time updates, improved productivity through the processing of multiple types of data, and better worker compliance with safety protocols by providing real time or near real time monitoring of personal protective equipment use, qualifications, and training for a variety of activities.

The safety communicator 150 may interact with one or more sensors to provide the information to the system 100. The sensors can include sensors associated with an individual (e.g., a portable sensor) and/or facility sensors (e.g., wireless or wired sensors including stationary sensors). In general, the individuals may wear one or more personal protection equipment (PPE) devices for detection and communication. For example, a person may wear a portable chemical detector operable to identify gases in the air and determine the levels of chemicals in the environment. The portable chemical sensor may comprise an array of sensors to measure a plurality of chemicals. Also, a person may wear any number of monitoring devices that may monitor movement, breathing, heart rate, etc. Additionally, personnel may wear portable location devices operable to communicate the location of the device (and therefore the user) to a central monitoring station. These portable devices may communicate wirelessly, over a wireless fidelity (Wi-Fi) network, via Bluetooth, or another wireless connection.

Facility sensors, which may be stationary within a facility, may also be present. The stationary sensors can measure any of the information that the portable and personal sensors can measure. The stationary sensors may also measure information such as environmental data (e.g., pressure, temperature, wind speed, wind direction, etc.). The facility sensors may communicate wirelessly and/or through a wired connection to the data analytics server 102 and/or the safety communicator 150 to provide data used with the applications 110.

In some cases, the multiple PPE devices associated with an individual may have alarms, notifications, or updates that are communicated to the user via sounds, vibrations, or visual notifications. In some embodiments, each PPE device may communicate individually with the central monitoring station, employing multiple wireless infrastructures. In some embodiments, a safety communicator 150 (e.g., a communication device) comprising a data collection and communication application may be used to collect the sensor data and communicate the sensor data to the various elements of the system 100. For example, the application may establish a connection between the smartphone and each of the PPE devices, which may be wireless connections, such as Wi-Fi or Bluetooth. The application may then receive data from each of the PPE devices, and store the data locally on the device. The application may also transfer the data to a cloud storage network via a cellular network. Additionally, the application may communicate the combined data from all of the PPE devices to the central monitoring station. The application may automatically receive data from the PPE devices and send the data to the data analytics server 102.

Additionally, the application may be operable to send messages or calls to other safety communicators associated with other individuals if needed, such as in an alarm or emergency situation.

The application on the safety communicator 150 may present information to the user via a user interface on the smartphone or connected to the smartphone (such as a smartwatch). The interface may compile the information received from each of the PPE devices into a consistent format, making it easier to read and understand. The user may be able to adjust alarm limits and settings in the application. The application may show real-time readings via the user interface, and may issue alerts or warnings via the user interface. Additionally, vibrations or audible alerts may also be issued by the application via the smartphone. In some cases, the application may be operable to communicate with a headset or earpiece (such as a Bluetooth headset for example) worn by the user to communicate audible alerts or warnings.

The sensors can detect various types of information such as chemical components of an environment, environmental conditions (e.g., temperature, pressure, wind speed, wind direction, etc.), vibration levels, noise levels, biometric parameters (e.g., heart rate, body temperature, respiration rate, etc.), location (e.g., including 2-dimensional and/or 3-dimensional position), and the like. The chemical sensors can be detected using various types of gas sensors. The gas detectors may include, but are not limited to, radiation detectors, smoke detectors, and detectors for determining abnormally low oxygen content in the atmosphere, as well as a wide variety of detectors for detecting chemically hazardous or flammable gases such as, for example, hydrogen sulfide, ammonia, carbon monoxide, natural gas, phosgene, organic compounds (e.g., volatile organic compounds, etc.), and so forth. The gas sensors can also be configured to include integrated wireless communications and the ability to periodically and under event conditions, report the location information, time information, and gas concentration level information wirelessly.

The use of multiple exposure values to determine a risk value may find applications in several areas. In an embodiment, the multiple sensor inputs from the chemical sensors can be used to determine the presence of an unmeasured chemical component. In an embodiment, one or more of the sensors may be targeted to a specific compound. However, chemical sensors can also exhibit cross-sensitivity from other compounds present in the environment. For example, hydrogen sulfide sensors can exhibit a cross-sensitivity reading from other chemicals such as carbon monoxide. For example, a carbon monoxide concentration of 10 ppm may produce a 1 ppm response in a typical hydrogen sulfide sensor. The sensors are generally designed so that the cross-sensitivity to a non-detected compound is significantly less than the sensitivity to the compound that the sensor is designed to detect. In an embodiment, a ratio of a portion of the sensor output resulting from the target compound or compounds (e.g., a mixture such as an explosive gas mixture, etc.) to a portion of the sensor output resulting from an unmeasured and cross-interfering compounds can be at least about 2:1, at least about 5:1, at least about 10:1, at least about 100:1 or at least about 1,000:1. In some embodiments, the ratio of the portion of the sensor output resulting from the target compound or compounds to the portion of the sensor output resulting from an unmeasured and cross-interfering compounds can be less than about 10,000:1 such that the cross-interference generates a measurable portion of the signal that can be used to pattern match the presence of any unmeasured compounds.

Each additional chemical in the environment may have an effect on the sensor readings, and the value of the cross-sensitivity for each chemical may be unique to the sensor and the chemical component. When multiple different chemical sensors are used, the cross-sensitivity patterns may provide patterns that can give an indication of the presence of an unmeasured chemical. For example, a multi-sensor array having a hydrogen sulfide sensor, a carbon monoxide sensor, and an ammonia sensor may each provide a cross-sensitivity value for an unknown compound. By detecting a potential cross-sensitivity pattern and matching the pattern to a database of known patterns for the specific compounds, one or more unknown compounds can be detected.

The cross-sensitivity patterns can be stored in the chemical pattern data store 122. The initial patterns can be determined in a number of ways. Since the cross-sensitivity is specific to the construction of each sensor, the sensors can be used individually or in groups to detect cross-sensitivity values for a plurality of chemicals. In an embodiment, the sensor or sensors can be exposed in controlled environments to known gas concentrations, either to individual gases or mixtures having known component concentration values. For example, each of the sensors can be exposed to an organic compound such as benzene to determine the cross-sensitivity effects. In general, the relative cross-sensitivity between sensors may be used to identify the chemical, and the magnitude of the cross-sensitivity may be used to determine the concentration of the chemical. The relative cross-sensitivity can be measured as ratios of the cross-sensitivity of each sensor to each other sensor and/or as relative percentages of sensitivity values. The resulting patterns from the initial data can be stored in the pattern data store 122. In some embodiments, the sensors can be exposed to combinations of chemicals to determine the combined effects of various expected combinations of unmeasured and/or measured chemicals in the case that the cross-sensitivity patterns do not have linear cross-sensitivity effects. For example, combinations of benzene, toluene, and xylene may be used to determine the relative cross-sensitivity for a variety of sensor if these chemicals are expected to be present together in an environment.

The pattern information data in the pattern data store 122 can be used based on the measurements, or various types of learning algorithms can be used to develop pattern models. For example, statistical models, neural networks (e.g., probabilistic neural networks, etc.), and the like can be used to receive the patterns from the chemical testing and create a model for matching the patterns to specific chemicals and chemical concentrations. For example, the known patterns can serve as training data to initially set up and establish the models and parameters used in the modes. The models may be used to extend the application of the patterns beyond those of the explicitly measured cross-sensitivity values and/or used to interpolate the cross-sensitivity values for combinations of chemicals that are not explicitly detected. The model, the model parameters, and various other information used with such models can be stored in the pattern data store 122 and used by the exposure application 112.

In some embodiments, the exposure application 112 can operate on the safety communicator 150 in order to provide real time or near real time information on the exposure values at the workers location. In this embodiment, the patterns and/or model and parameters can be sent to the safety communicator 150 at various intervals to allow the exposure application 112 to operate on the safety communicator 150. By having the exposure application 112 operate on the safety communicator 150, the detected chemicals can be determined in real time or near real time even if a network communication link is not present.

During use of the system 100, the chemical readings from each of the one or more sensors 152, 154 can be received and used by the safety communicator 150 and/or the exposure application 112 on the data analytics server 102 to determine the value of the measured chemicals. In addition, the exposure application 112 may detect a pattern of cross-sensitivity from one or more additional chemicals based on the chemical sensor readings. The exposure application 112 may first determine the cross-sensitivity readings for each chemical sensor. One or more aspects of the cross-sensitivity readings can be determined such as the relative values for each sensor, the magnitude of each cross-sensitivity value, and the like. The cross-sensitivity readings can then be compared to one or more patterns to determine the identity of one or more unmeasured chemicals that may be present in the environment. In general, the pattern data can include the relative cross-sensitivity amongst particular sensors to one or more chemicals. As described in more detail below, the patterns can also include statistical model parameters or data to allow the patterns to be matched to one or more specific chemicals. The pattern data can be obtained from the pattern data store 122 and used to detect the presence, and optionally, the concentration of one or more additional chemicals in the environment. The presence of the one or more unmeasured compounds and the concentration of the compounds can be used in various ways.

In some embodiments, historical data from the historical data store 126 can include measurements of chemicals at various locations in a facility. For example, gas samples can be measured at various locations in a facility over time and analyzed using various techniques such as gas chromatography. The resulting analysis may provide an indication of the types of chemicals present at a given location. In other embodiments, the process model may provide an indication of the chemicals present at various locations in a facility. Other information such as environmental conditions (e.g., wind direction, wind speed, etc.) and the like can be used to provide a prediction of the types of chemicals that can expected at various locations. This information can be accessed by the exposure application to identify a list of one or more chemicals that may be present at the location of the sensors 152, 154. The list of expected chemicals can then be used as a starting point for analyzing the sensor readings to determine which chemicals from the list may be present based on the cross-sensitivity of each chemical on the list. The use of the historical and prediction data may improve the prediction of the unmeasured compounds by narrowing the total number of sources and potential compounds present for the analysis of the cross-sensitivity values.

The exposure application 112 may output a list of one or more chemicals present in the environment. The list may include the detected chemicals that are directly measured by the sensors 152, 154. The list may also include one or more chemicals that are not directly measured (e.g., the unmeasured chemicals) based on the analysis of the cross-sensitivity values. The exposure application 112 can use the determined identity and concentrations of the unmeasured chemicals in a number of ways. For example, the exposure application 112 may use the chemical identity and concentrations to reduce or eliminate the cross-sensitivity values from the readings of the measured chemicals. For example, the detected cross-sensitivity readings can be eliminated from the measured chemicals to provide a more accurate reading of the chemicals detected by the sensors. This may provide improved safety warnings as well as reduce potentially false alarms based on increased readings resulting from cross-sensitivity. In this embodiment, the identity and concentration of the unmeasured compound can be determined and the cross-interference for the identified compound can be calculated. The calculated cross-interference can then be provided with the measurement from the sensor to provide a corrected output that accounts for the presence and cross-interference effects of the unmeasured compound. The determination of the unmeasured chemicals and their concentrations can also be used to provide exposure values for the workers, as described in more detail below.

In some embodiments, a learning algorithm may be used to update the patterns in the pattern data store 122. Over time, and regardless of where the exposure application executes, the sensor readings from the sensors 152, 154 can be stored in the sensor data store 124. In addition to the data from the sensors, the sensor data store 124 can include sensor readings for the facility from additional sensors or inputs such as gas sampling data. In some embodiments, the same type of sensor may be present at the facility as a stationary or portable sensor. The sensor may have a different construction while sensing the same type of chemical and as a result provide a different cross-sensitivity reading for the same type of unmeasured chemical. In this instance, the sensor data may have different readings that can be used to improve the pattern. In some embodiments, specific sensors may measure compounds that are not detected by a multi sensor array. For example, a stationary sensor array may detect additional chemicals not detected by a portable sensor array. In this embodiment, the stationary sensor readings can be used to improve the patterns for the portable sensor arrays.

The exposure application 112 may periodically use the sensor data from the sensors 152, 154 in combination with the data from other sensors to perform an analysis of the sensor readings and chemicals present in the environment to update the existing patterns and/or develop new patterns. The new patterns can include patterns for new chemicals that may be present and/or patterns for combinations of chemicals. In some embodiments, the updated analysis may be performed using data from across various facilities. For example, a sensor manufacturer may collect sensor readings across multiple facilities and use the exposure application 112 to perform a pattern update. The resulting update can then be sent to one or more facilities using the respective sensors. The updated analysis can be performed continuously, periodically, and/or at discrete times. Once received, the facilities can update the sensors and models used at the facility. This may allow data from one facility or location to be used in models and sensors at different facilities.

When the patterns are updated at a given facility and/or using data from a different facility or source, the updated patterns can be stored in the pattern data store 122. When the exposure application 112 executes on a local device such as the safety communicator 150, the patterns can be sent to the safety communicator 150 for performing the cross-sensitivity analysis. This may allow for an improved determination of the presence and concentration of one or more chemicals that are not directly measured by a plurality of chemical sensors.

The exposure application 112 may provide a dynamic mapping of a facility to determine if any areas have unacceptable exposure levels for an individual for the measured and/or unmeasured chemicals. Using the mapping, the exposure application 112 can determine the acceptable thresholds throughout an area. The acceptable exposure levels as well as alerts and notifications can be sent from the exposure application 112 to the safety communicator 150 for display to each individual. In some embodiments, the acceptable threshold and/or mapping can be sent to the safety communicator 150, which can perform the determination of the presence of the unmeasured chemicals for the individual.

The exposure application 112 may proactively use the exposure determination for the measured and/or unmeasured chemicals in the facility to suggest or require certain PPE for an individual. In some embodiments, the type of PPE being used by an individual can be stored in the personal protective equipment (PPE) data store 128 along with specific information for various types of PPE. For example, the safety communicator 150 may be capable of detecting the presence of various PPE as well as compliance with the proper use of the PPE by the individual within the facility. PPE information for each of the PPE being used can be obtained from the PPE data store 128 for use with the exposure application 112. For example, a type of respirator may be detected by the safety communicator 150 including the proper positioning of the respirator as well as a model number or other identifier for the respirator. Using the identifier, the level and type of chemical protection can be retrieved from the PPE data store 128 and used in the determination of the individual exposure threshold.

This determination of the exposure level to the measured and/or unmeasured chemicals may be determined for each person present within a facility. The system 100 may continue to update the exposure values over time to provide real time or near real time updates to the workers. The updated exposure levels can be checked against the current individual's location, PPE usage, training, and the like to determine if exposure level exceeds the applicable thresholds for the specific worker. If any threshold is violated, a notification, alert, warning, or other indication can be sent to the individual (e.g., to the safety communicator 150) and/or a manager or supervisor. The indication may provide updated requirements for working in the affected areas. For example, when it is determined that an unmeasured chemical exceeds the exposure threshold, a warning on the presence of the chemical as well as exposure level can be sent to the safety communicator. The warning can include a notification to use a different type of PPE. For example, a respirator capable of removing organic compounds may be required even if organics are not expected in the area and are not directly measured. This may provide an improved detection and safety notification system for workers at a facility.

Figure 2:
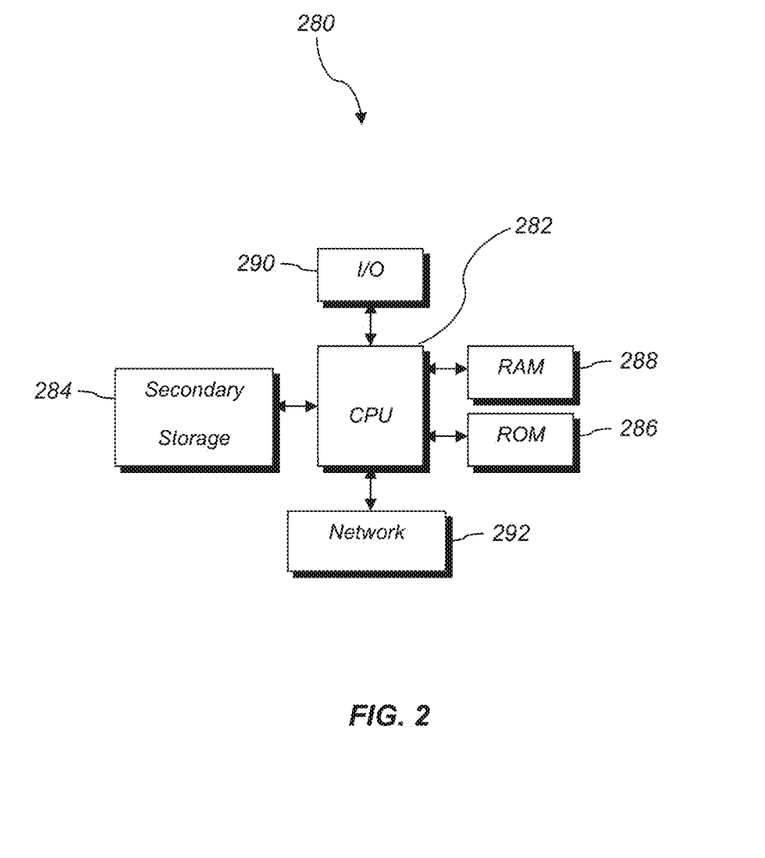
FIG. 2 schematically illustrates a computer that can be used to carry out various steps according to an embodiment.

Any of the systems and methods disclosed herein can be carried out on a computer or other device comprising a processor, such as the communication device 150, the data analytics server 102, any of the sensors 152, 154, and/or the database 120 of FIG. 1. FIG. 2 illustrates a computer system 280 suitable for implementing one or more embodiments disclosed herein such as the acquisition device or any portion thereof. The computer system 280 includes a processor 282 (which may be referred to as a central processor unit or CPU) that is in communication with memory devices including secondary storage 284, read only memory (ROM) 286, random access memory (RAM) 288, input/output (I/O) devices 290, and network connectivity devices 292. The processor 282 may be implemented as one or more CPU chips.

It is understood that by programming and/or loading executable instructions onto the computer system 280, at least one of the CPU 282, the RAM 288, and the ROM 286 are changed, transforming the computer system 280 in part into a particular machine or apparatus having the novel functionality taught by the present disclosure. It is fundamental to the electrical engineering and software engineering arts that functionality that can be implemented by loading executable software into a computer can be converted to a hardware implementation by well-known design rules. Decisions between implementing a concept in software versus hardware typically hinge on considerations of stability of the design and numbers of units to be produced rather than any issues involved in translating from the software domain to the hardware domain. Generally, a design that is still subject to frequent change may be preferred to be implemented in software, because re-spinning a hardware implementation is more expensive than re-spinning a software design. Generally, a design that is stable that will be produced in large volume may be preferred to be implemented in hardware, for example in an application specific integrated circuit (ASIC), because for large production runs the hardware implementation may be less expensive than the software implementation. Often a design may be developed and tested in a software form and later transformed, by well-known design rules, to an equivalent hardware implementation in an application specific integrated circuit that hardwires the instructions of the software. In the same manner as a machine controlled by a new ASIC is a particular machine or apparatus, likewise a computer that has been programmed and/or loaded with executable instructions may be viewed as a particular machine or apparatus.

Additionally, after the system 280 is turned on or booted, the CPU 282 may execute a computer program or application. For example, the CPU 282 may execute software or firmware stored in the ROM 286 or stored in the RAM 288. In some cases, on boot and/or when the application is initiated, the CPU 282 may copy the application or portions of the application from the secondary storage 284 to the RAM 288 or to memory space within the CPU 282 itself, and the CPU 282 may then execute instructions that the application is comprised of. In some cases, the CPU 282 may copy the application or portions of the application from memory accessed via the network connectivity devices 292 or via the I/O devices 290 to the RAM 288 or to memory space within the CPU 282, and the CPU 282 may then execute instructions that the application is comprised of. During execution, an application may load instructions into the CPU 282, for example load some of the instructions of the application into a cache of the CPU 282. In some contexts, an application that is executed may be said to configure the CPU 282 to do something, e.g., to configure the CPU 282 to perform the function or functions promoted by the subject application. When the CPU 282 is configured in this way by the application, the CPU 282 becomes a specific purpose computer or a specific purpose machine.

The secondary storage 284 is typically comprised of one or more disk drives or tape drives and is used for non-volatile storage of data and as an over-flow data storage device if RAM 288 is not large enough to hold all working data. Secondary storage 284 may be used to store programs which are loaded into RAM 288 when such programs are selected for execution. The ROM 286 is used to store instructions and perhaps data which are read during program execution. ROM 286 is a non-volatile memory device which typically has a small memory capacity relative to the larger memory capacity of secondary storage 284. The RAM 288 is used to store volatile data and perhaps to store instructions. Access to both ROM 286 and RAM 288 is typically faster than to secondary storage 284. The secondary storage 284, the RAM 288, and/or the ROM 286 may be referred to in some contexts as computer readable storage media and/or non-transitory computer readable media.

I/O devices 290 may include printers, video monitors, liquid crystal displays (LCDs), touch screen displays, keyboards, keypads, switches, dials, mice, track balls, voice recognizers, card readers, paper tape readers, or other well-known input devices.

The network connectivity devices 292 may take the form of modems, modem banks, Ethernet cards, universal serial bus (USB) interface cards, serial interfaces, token ring cards, fiber distributed data interface (FDDI) cards, wireless local area network (WLAN) cards, radio transceiver cards that promote radio communications using protocols such as code division multiple access (CDMA), global system for mobile communications (GSM), long-term evolution (LTE), worldwide interoperability for microwave access (WiMAX), near field communications (NFC), radio frequency identity (RFID), and/or other air interface protocol radio transceiver cards, and other well-known network devices. These network connectivity devices 292 may enable the processor 282 to communicate with the Internet or one or more intranets. With such a network connection, it is contemplated that the processor 282 might receive information from the network, or might output information to the network (e.g., to an event database) in the course of performing the above-described method steps. Such information, which is often represented as a sequence of instructions to be executed using processor 282, may be received from and outputted to the network, for example, in the form of a computer data signal embodied in a carrier wave.

Such information, which may include data or instructions to be executed using processor 282 for example, may be received from and outputted to the network, for example, in the form of a computer data baseband signal or signal embodied in a carrier wave. The baseband signal or signal embedded in the carrier wave, or other types of signals currently used or hereafter developed, may be generated according to several methods well-known to one skilled in the art. The baseband signal and/or signal embedded in the carrier wave may be referred to in some contexts as a transitory signal.

The processor 282 executes instructions, codes, computer programs, scripts which it accesses from hard disk, floppy disk, optical disk (these various disk based systems may all be considered secondary storage 284), flash drive, ROM 286, RAM 288, or the network connectivity devices 292. While only one processor 282 is shown, multiple processors may be present. Thus, while instructions may be discussed as executed by a processor, the instructions may be executed simultaneously, serially, or otherwise executed by one or multiple processors. Instructions, codes, computer programs, scripts, and/or data that may be accessed from the secondary storage 284, for example, hard drives, floppy disks, optical disks, and/or other device, the ROM 286, and/or the RAM 288 may be referred to in some contexts as non-transitory instructions and/or non-transitory information.

In an embodiment, the computer system 280 may comprise two or more computers in communication with each other that collaborate to perform a task. For example, but not by way of limitation, an application may be partitioned in such a way as to permit concurrent and/or parallel processing of the instructions of the application. Alternatively, the data processed by the application may be partitioned in such a way as to permit concurrent and/or parallel processing of different portions of a data set by the two or more computers. In an embodiment, virtualization software may be employed by the computer system 280 to provide the functionality of a number of servers that is not directly bound to the number of computers in the computer system 280. For example, virtualization software may provide twenty virtual servers on four physical computers. In an embodiment, the functionality disclosed above may be provided by executing the application and/or applications in a cloud computing environment. Cloud computing may comprise providing computing services via a network connection using dynamically scalable computing resources. Cloud computing may be supported, at least in part, by virtualization software. A cloud computing environment may be established by an enterprise and/or may be hired on an as-needed basis from a third party provider. Some cloud computing environments may comprise cloud computing resources owned and operated by the enterprise as well as cloud computing resources hired and/or leased from a third party provider.

In an embodiment, some or all of the functionality disclosed above may be provided as a computer program product. The computer program product may comprise one or more computer readable storage medium having computer usable program code embodied therein to implement the functionality disclosed above. The computer program product may comprise data structures, executable instructions, and other computer usable program code. The computer program product may be embodied in removable computer storage media and/or non-removable computer storage media. The removable computer readable storage medium may comprise, without limitation, a paper tape, a magnetic tape, magnetic disk, an optical disk, a solid state memory chip, for example analog magnetic tape, compact disk read only memory (CD-ROM) disks, floppy disks, jump drives, digital cards, multimedia cards, and others. The computer program product may be suitable for loading, by the computer system 280, at least portions of the contents of the computer program product to the secondary storage 284, to the ROM 286, to the RAM 288, and/or to other non-volatile memory and volatile memory of the computer system 280. The processor 282 may process the executable instructions and/or data structures in part by directly accessing the computer program product, for example by reading from a CD-ROM disk inserted into a disk drive peripheral of the computer system 280. Alternatively, the processor 282 may process the executable instructions and/or data structures by remotely accessing the computer program product, for example by downloading the executable instructions and/or data structures from a remote server through the network connectivity devices 292. The computer program product may comprise instructions that promote the loading and/or copying of data, data structures, files, and/or executable instructions to the secondary storage 284, to the ROM 286, to the RAM 288, and/or to other non-volatile memory and volatile memory of the computer system 280.

In some contexts, the secondary storage 284, the ROM 286, and the RAM 288 may be referred to as a non-transitory computer readable medium or a computer readable storage media. A dynamic RAM embodiment of the RAM 288, likewise, may be referred to as a non-transitory computer readable medium in that while the dynamic RAM receives electrical power and is operated in accordance with its design, for example during a period of time during which the computer system 280 is turned on and operational, the dynamic RAM stores information that is written to it. Similarly, the processor 282 may comprise an internal RAM, an internal ROM, a cache memory, and/or other internal non-transitory storage blocks, sections, or components that may be referred to in some contexts as non-transitory computer readable media or computer readable storage media.

EXAMPLES

The disclosure having been generally described, the following examples are given as particular embodiments of the disclosure and to demonstrate the practice and advantages thereof. It is understood that the examples are given by way of illustration and are not intended to limit the specification or the claims in any manner.

Example 1

Additional Gas Detection Without a Specific Sensor

A combination of sensors include a hydrogen sulfide ($H_2S$) sensor, a sulfur dioxide ($SO_2$) sensor, and a nitrogen dioxide ($NO_2$) sensor are considered to for detecting chlorine gas ($Cl_2$). $NO_2$ can have a negative cross-sensitivity with $H_2S$ and $SO_2$ sensors. The combination of all three sensors would allow for the measure of up to 3 gases simultaneously, and infer at least the presence and concentration of a fourth component. In this example, when 10 ppm of $Cl_2$ gas is applied to the sensors, the $NO_2$ sensor shows −10 ppm. When the gas mixture has 10 ppm $Cl_2$ and 10 ppm $SO_2$, then the $NO_2$ sensor shows −20 ppm, and the $SO_2$ sensor reads 10 ppm. The inferred chlorine concentration will be 10 ppm. Additionally, when the gas mixture has 10 ppm $Cl_2$, 10 ppm $SO_2$, and 50 ppm $H_2S$, the sensors will read: $H_2S$ is 50 ppm, $SO_2$ is 10 ppm, and NO2 −24 ppm. Based on these readings, the calculated $Cl_2$ concentration is 10 ppm. This information is illustrated in Table 1.

TABLE 1

| | | Sensors reading | | | Additional gas detected |
|---|---|---|---|---|---|
| Gas | Concentration | $H_2S$ | $SO_2$ | $NO_2$ | |
| single gas | $Cl_2$ | 10 ppm | 0 ppm | 0 ppm | −10 ppm | $Cl_2$ |
| mix 2 | $Cl_2$ | 10 ppm | | | | |
| | $SO_2$ | 10 ppm | 0 ppm | 10 ppm | −20 ppm | $Cl_2$ |
| mix 3 | $Cl_2$ | 10 ppm | | | | |
| | $SO_2$ | 10 ppm | | | | |
| | $H_2S$ | 50 ppm | 50 ppm | 10 ppm | −24 ppm | $Cl_2$ |

Thus, the presence of an unmeasured chemical is possible through the use of multiple chemical sensors, and the concentration can be determined based on the cross-sensitivity patterns.

Example 2

False Alarm and Reduction in Cross-Sensitivity Measurements

A combination of sensors include a hydrogen cyanide (HCN) sensor, a hydrogen sulfide ($H_2S$) sensor, and a sulfur dioxide ($SO_2$) sensor, are considered for detecting a cross-sensitivity between compounds. When $H_2S$ is present at a concentration of 5 ppm, the HCN sensor reading is 30 ppm, which indicates a false alarm situation since no HCN is present. When $H_2S$ is present at a concentration of 4 ppm and $SO_2$ is present at a concentration of 5 ppm, the HCN sensor reading is 43 ppm, again indicating a false alarm. When $H_2S$ is present at 3 ppm, $SO_2$ is present at 5 ppm, and HCN is present at 10 ppm, the HCN sensor reading is 47 ppm. The actual HCN concentration is just 10 ppm. This information is illustrated in Table 2.

TABLE 2

| | | | Sensors reading | | | False alarm |
|---|---|---|---|---|---|---|
| | Gas | Concentration | H2S | SO2 | HCN | |
| single gas | H2S | 5 ppm | 5 ppm | 0 ppm | 30 ppm | HCN |
| mix 2 | H2S | 4 ppm | | | | |
| | SO2 | 5 ppm | 4 ppm | 5 ppm | 43 ppm | HCN |
| mix 3 | H2S | 3 ppm | | | | |
| | SO2 | 5 ppm | | | | |
| | HCN | 10 ppm | 3 ppm | 5 ppm | 47 ppm | HCN* |

*real HCN concentration is 10 ppm

Thus, the cross-sensitivity patterns can be used to identify the potential readings caused by the cross-sensitivity and detect an actual gas concentration in the surrounding gas. The cross-sensitivity can then be eliminated based on the patterns to avoid false alarms and present a more accurate measurement of the gases present.

Having described various systems and methods herein, a number of embodiments can include, but are not limited to:

In a first embodiment, a method of determining the presence of an unmeasured chemical in an environment comprises receiving, by an exposure application stored in a non-transitory memory and executed on a processor, a plurality of sensor readings from a plurality of chemical sensors, wherein each chemical sensor of the plurality of chemical sensors is configured to detect a different chemical; determining, by the exposure application, a cross-sensitivity pattern from one or more unmeasured chemicals in the plurality of sensor readings; comparing, by the exposure application, the cross-sensitivity pattern with one or more known chemical patterns; determining that the cross-sensitivity pattern matches at least one of the one or more known chemical patterns, wherein the one or more known chemical patterns correspond to one or more chemicals; and identifying one or more unmeasured chemicals based on determining that the cross-sensitivity pattern matches the at least one of the one or more known chemical patterns.

A second embodiment can include the method of the first embodiment, further comprising: determining a representation of the cross-sensitivity pattern; and determining a concentration of the one or more unmeasured chemicals based on the representation of the cross-sensitivity pattern.

A third embodiment can include the method of the second embodiment, further comprising: determining a cross-sensitivity from the one or more unmeasured chemicals and the concentration of the one or more unmeasured chemicals; and removing the cross-sensitivity from the plurality of sensor readings.

A fourth embodiment can include the method of any of the first to third embodiments, further comprising: determining a concentration of one or more measured chemicals based on the plurality of sensor readings.

A fifth embodiment can include the method of any of the second to fourth embodiments, further comprising: comparing the concentration of the one or more unmeasured chemicals to corresponding thresholds for the one or more unmeasured chemicals; and providing an alert when the concentration of at least one of the one or more unmeasured chemicals exceeds the corresponding threshold.

A sixth embodiment can include the method of the first embodiment, further comprising: determining, by the exposure application, at least one personal protective equipment requirement based on the identification of the one or more unmeasured chemicals.

A seventh embodiment can include the method of any of the first to sixth embodiments, further comprising: determining an identification of chemicals present in an area, wherein the one or more known chemical patterns include chemical patterns for the chemicals on the identification of the chemicals.

An eighth embodiment can include the method of any of the first to sixth embodiments, further comprising: determining an identification of chemicals present in an area, wherein the one or more known chemical patterns include chemical patterns only for the chemicals in the identification of the chemicals.

A ninth embodiment can include the method of any of the first to eighth embodiments, further comprising: receiving, by the exposure application from one or more additional sensors, at least one measured value of the one or more unmeasured chemicals; correlating the at least one measured value for the one or more unmeasured chemicals with a determined concentration of the one or more unmeasured chemicals; and updating the one or more known chemical patterns based on the correlating.

In a tenth embodiment, a chemical compound measurement system comprises a memory storing an exposure application; a pattern store storing known chemical patterns, and a processor, wherein the exposure application, when executed on the processor, configures the processor to: receive a plurality of sensor readings from a plurality of chemical sensors, wherein each chemical sensor of the plurality of chemical sensors is configured to detect a different chemical; determine a cross-sensitivity pattern from one or more unmeasured chemicals in the plurality of sensor readings; compare the cross-sensitivity pattern with one or more of the known chemical patterns; determine that the cross-sensitivity pattern matches at least one of the one or more known chemical patterns, wherein the one or more known chemical patterns correspond to one or more chemicals; and identify one or more unmeasured chemicals based on determining that the cross-sensitivity pattern matches the at least one of the one or more known chemical patterns.

An eleventh embodiment can include the system of the tenth embodiment, wherein the exposure application, when executed on the processor, further configures the processor to: determine a representation of the cross-sensitivity pattern; and determine a concentration of the one or more unmeasured chemicals based on the representation of the cross-sensitivity pattern.

A twelfth embodiment can include the system of the eleventh embodiment, wherein the exposure application, when executed on the processor, further configures the processor to: determine an expected cross-sensitivity from the one or more unmeasured chemicals and the concentration of the one or more unmeasured chemicals; and remove the expected cross-sensitivity from the plurality of sensor readings.

A thirteenth embodiment can include the system of the eleventh embodiment, wherein the exposure application, when executed on the processor, further configures the processor to: compare the concentration of the one or more unmeasured chemicals to corresponding thresholds for the one or more unmeasured chemicals; and provide an alert when the concentration of at least one of the one or more unmeasured chemicals exceeds the corresponding threshold.

A fourteenth embodiment can include the system of the tenth embodiment, wherein the exposure application, when executed on the processor, further configures the processor to: receive, from one or more additional sensors, at least one measured value of the one or more unmeasured chemicals; correlate the at least one measured value for the one or more unmeasured chemicals with a determined concentration of the one or more unmeasured chemicals; and update the one or more known chemical patterns based on the correlating.

A fifteenth embodiment can include the system of the tenth embodiment, wherein the exposure application, when executed on the processor, further configures the processor to: determine at least one personal protective equipment requirement based on the identification of the one or more unmeasured chemicals.

In a sixteenth embodiment, a method of determining the presence of a compound in an environment comprises receiving a plurality of sensor outputs from a plurality of chemical sensors, wherein each chemical sensor of the plurality of chemical sensors is configured to detect a different chemical, wherein a ratio of a first portion of each of the sensor outputs resulting from a detected compound to a second portion of the sensor output resulting from an unmeasured compound is at least about 2:1; determining a cross-sensitivity pattern resulting from the presence of the unmeasured compound using the plurality of sensor outputs; comparing the cross-sensitivity pattern with one or more known chemical patterns; determining that the cross-sensitivity pattern matches at least one of the one or more known chemical patterns, wherein the one or more known chemical patterns correspond to one or more compounds; and identifying the unmeasured compound based on determining that the cross-sensitivity pattern matches the at least one of the one or more known chemical patterns.

A seventeenth embodiment can include the method of the sixteenth embodiment, further comprising: determining a representation of the cross-sensitivity pattern; and determining a concentration of the unmeasured compound based on the representation of the cross-sensitivity pattern.

An eighteenth embodiment can include the method of the seventeenth embodiment, further comprising: determining, for one or more of the plurality of chemical sensors, a cross-sensitivity from the unmeasured compound and the concentration of the unmeasured compound; and removing the cross-sensitivity from one or more of the plurality of sensor outputs.

A nineteenth embodiment can include the method of the seventeenth embodiment, further comprising: comparing the concentration of the unmeasured compound to a corresponding threshold for the unmeasured compound; and providing an alert when the concentration of the unmeasured compound exceeds the corresponding threshold.

A twentieth embodiment can include the method of the sixteenth embodiment, further comprising: receiving at least one measured value of the unmeasured compound; correlating the at least one measured value for the unmeasured compound with a determined concentration of the unmeasured compound; and updating the one or more known chemical patterns based on the correlating.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. A method of determining a personal protective equipment requirement due to a determination of a presence of a chemical or combination of chemicals in an environment, the method comprising:
receiving, by an exposure application stored in a non-transitory memory and executed on a processor, a plurality of sensor readings from a plurality of chemical sensors via a communication device associated with an individual, wherein each chemical sensor of the plurality of chemical sensors is configured to detect a different chemical;
determining, by the exposure application, a cross-sensitivity pattern from the plurality of sensor readings;
comparing, by the exposure application, the cross-sensitivity pattern with one or more known chemical patterns, each of the one or more known chemical patterns corresponding to a known chemical or a known combination of chemicals;
determining that the cross-sensitivity pattern matches one of the one or more known chemical patterns;
identifying a chemical or combination of chemicals giving rise to the cross-sensitivity pattern based on determining that the cross-sensitivity pattern matches the one of the one or more known chemical patterns;
determining, by the exposure application, a current type of personal protective equipment associated with the individual;
determining compliance with a proper positioning of the personal protective equipment associated with the individual;
determining, by the exposure application, in real time or near real time, an exposure threshold level for the individual based on the determined current type of personal protective equipment, the determined compliance with the proper positioning of the personal protective equipment associated with the individual, and the identification of the chemical or combination of chemicals giving rise to the cross-sensitivity pattern;
monitoring, by the exposure application, an exposure value of the individual to the identified chemical or combination of chemicals giving rise to the cross-sensitivity pattern;
comparing the monitored exposure value of the individual with the determined exposure threshold level for the individual, wherein the monitored exposure value of the individual is determined based on a current location of the individual and an expected location of the individual, and wherein the expected location of the individual depends upon a predictive movement of the individual present in an area of the environment; and
upon determining that the monitored exposure value of the individual exceeds the exposure threshold value, determining a new personal protective equipment requirement for at least one different type of personal protective equipment for the individual and sending a notification to use the at least one different type of personal protective equipment to the communication device associated with the individual.

2. The method of claim 1, further comprising:
determining a concentration of the chemical or combination of chemicals based on the cross-sensitivity pattern.

3. The method of claim 2, further comprising:
determining a cross-sensitivity due to the presence of the chemical or combination of chemicals giving rise to the cross-sensitivity pattern and the concentration of the chemical or combination of chemicals giving rise to the cross-sensitivity pattern; and
removing the cross-sensitivity from the plurality of sensor readings.

4. The method of claim 1, further comprising:
determining a concentration of one of the chemicals based on the sensor reading from the chemical sensor configured to detect said one of the chemicals.

5. The method of claim 1, further comprising:
comparing a concentration of the chemical or combination of chemicals giving rise to the cross-sensitivity pattern to a corresponding threshold for the chemical or combination of chemicals giving rise to the cross-sensitivity pattern, wherein the corresponding threshold for the chemical or combination of chemicals giving rise to the cross-sensitivity pattern is based at least in part on the determined current level of personal protective equipment associated with the individual; and
providing an alert when the concentration of the chemical or combination of chemicals giving rise to the cross-sensitivity pattern exceeds the corresponding threshold.

6. The method of claim 1, further comprising:
determining a list of chemicals that may be present at a location of the plurality of chemical sensors, wherein the one or more known chemical patterns include chemical patterns for the chemicals in the list.

7. The method of claim 1, further comprising:
determining a list of chemicals that may be present at a location of the plurality of chemical sensors, wherein the one or more known chemical patterns include chemical patterns only for the chemicals in the list.

8. The method of claim 1, further comprising:
determining, based on the cross-sensitivity pattern, a concentration of the chemical or combination of chemicals giving rise to the cross-sensitivity pattern;
receiving, by the exposure application from one or more additional sensors, at least one measured value of the chemical or combination of chemicals giving rise to the cross-sensitivity pattern;
correlating the at least one measured value for the chemical or combination of chemicals giving rise to the cross-sensitivity pattern with the determined concentration of the chemical or combination of chemicals giving rise to the cross-sensitivity pattern; and
updating the one or more known chemical patterns based on the correlating.

9. The method of claim 1, further comprising:
receiving a current location of the individual;
receiving a current location associated with a second individual;

determining an expected location of the second individual based at least in part on the current location associated with the second individual and predicted movements associated with the second individual;

determining a current type of personal protective equipment associated with the second individual;

determining, by the exposure application, in real time or near real time, at least one different type of personal protective equipment associated with the second individual based on the current location and the expected location of the second individual, the determined current type of personal protective equipment associated with the second individual, and the identification of the chemical or combination of chemicals giving rise to the cross-sensitivity pattern; and sending a notification of the at least one determined different type of personal protective equipment associated with the second individual to a communication device associated with the second individual.

10. The method of claim 1, wherein determining, by the exposure application, the current type of personal protective equipment associated with the individual comprises:

detecting an identifier of the personal protective equipment associated with the individual; and based at least in part on the identifier, retrieving the current type of personal protective equipment associated with the individual from a personal protective equipment datastore.

11. A chemical compound measurement system, the system comprising:

a memory storing an exposure application;

a pattern store storing known chemical patterns, each of the known chemical patterns corresponding to a known chemical or a known combination of chemicals, and a processor, wherein the exposure application, when executed on the processor, configures the processor to:

receive a plurality of sensor readings from a plurality of chemical sensors via a communication device associated with an individual, wherein each chemical sensor of the plurality of chemical sensors is configured to detect a different chemical;

determine a cross-sensitivity pattern from the plurality of sensor readings;

compare the cross-sensitivity pattern with one or more of the known chemical patterns;

determine that the cross-sensitivity pattern matches one of the known chemical patterns;

identify a chemical or combination of chemicals giving rise to the cross-sensitivity pattern based on determining that the cross-sensitivity pattern matches the one of the known chemical patterns;

determine a current type of personal protective equipment associated with the individual;

determine compliance with a proper positioning of the personal protective equipment associated with the individual;

determine, in real time or near real time, an exposure threshold level for the individual based on the determined current type of personal protective equipment, the determined compliance with the proper positioning of the personal protective equipment associated with the individual, and the identification of the chemical or combination of chemicals giving rise to the cross-sensitivity pattern;

monitor an exposure value of the individual to the identified chemical or combination of chemicals giving rise to the cross-sensitivity pattern;

compare the monitored exposure value of the individual with the determined exposure threshold level for the individual, wherein the monitored exposure value of the individual is determined based on a current location of the individual and an expected location of the individual, and wherein the expected location of the individual depends upon a predictive movement of the individual present in an area of the environment; and upon determination that the monitored exposure value of the individual exceeds the exposure threshold value, determine a new personal protective equipment requirement for at least one different type of personal protective equipment for the individual and send a notification to use the at least one different type of personal protective equipment to the communication device associated with the individual.

12. The system of claim 11, wherein the exposure application, when executed on the processor, further configures the processor to:

determine a concentration of the chemical or combination of chemicals giving rise to the cross-sensitivity pattern based on the cross-sensitivity pattern.

13. The system of claim 12, wherein the exposure application, when executed on the processor, further configures the processor to:

determine a cross-sensitivity due to the presence of the chemical or combination of chemicals giving rise to the cross-sensitivity pattern and the concentration of the chemical or combination of chemicals giving rise to the cross-sensitivity pattern; and remove the cross-sensitivity from the plurality of sensor readings.

14. The system of claim 11, wherein the exposure application, when executed on the processor, further configures the processor to;

compare a concentration of the chemical or combination of chemicals giving rise to the cross-sensitivity pattern to a corresponding threshold for the chemical or combination of chemicals giving rise to the cross-sensitivity pattern; and provide an alert when the concentration of the chemical or combination of chemicals giving rise to the cross-sensitivity pattern exceeds the corresponding threshold.

15. The system of claim 11, wherein the exposure application, when executed on the processor, further configures the processor to:

determine, based on the cross-sensitivity pattern, a concentration of the chemical or combination of chemicals giving rise to the cross-sensitivity pattern;

receive, from one or more additional sensors, at least one measured value of the chemical or combination of chemicals giving rise to the cross-sensitivity pattern;

correlate the at least one measured value for the chemical or combination of chemicals giving rise to the cross-sensitivity pattern with the determined concentration of the chemical or combination of chemicals giving rise to the cross-sensitivity pattern; and update the one or more known chemical patterns based on the correlating.

16. A method of determining a personal protective equipment requirement due to a determination of the presence of a chemical or combination of chemicals in an environment, the method comprising:

receiving a plurality of sensor outputs from a plurality of chemical sensors via a communication device associated with an individual, wherein each chemical sensor of the plurality of chemical sensors is configured to detect a different target chemical, and wherein each chemical sensor of the plurality of chemical sensors is configured such that a sensitivity reading to a target chemical is at least two times a cross-sensitivity reading to a non-target chemical or combination of chemicals;

determining a cross-sensitivity pattern from the plurality of sensor outputs;

comparing the cross-sensitivity pattern with one or more known chemical patterns, each of the one or more known chemical patterns corresponding to a known chemical or a known combination of chemicals;

determining that the cross-sensitivity pattern matches one of the one or more known chemical patterns;

identifying a chemical or combination of chemicals giving rise to the cross-sensitivity pattern based on determining that the cross-sensitivity pattern matches the one of the one or more known chemical patterns;

determining a current type of personal protective equipment associated with the individual;

determining compliance with a proper positioning of the personal protective equipment associated with the individual;

determining, in real time or near real time, an exposure threshold level for the individual based on the determined current type of personal protective equipment, the determined compliance with the proper positioning of the personal protective equipment associated with the individual, and the identification of the chemical or combination of chemicals giving rise to the cross-sensitivity pattern;

monitoring an exposure value of the individual to the identified chemical or combination of chemicals giving rise to the cross-sensitivity pattern;

comparing the monitored exposure value of the individual with the determined exposure threshold level for the individual, wherein the monitored exposure value of the individual is determined based on a current location of the individual and an expected location of the individual, and wherein the expected location of the individual depends upon a predictive movement of the individual present in an area of the environment; and upon determining that the monitored exposure value of the individual exceeds the exposure threshold value, determining a new personal protective equipment requirement for at least one different type of personal protective equipment for the individual and sending a notification to use the at least one different type of personal protective equipment to the communication device associated with the individual.

17. The method of claim 16, further comprising:
determining a concentration of the chemical or combination of chemicals based on the cross-sensitivity pattern.

18. The method of claim 17, further comprising:
determining, for one or more of the plurality of chemical sensors, a cross-sensitivity due to a presence of the chemical or combination of chemicals giving rise to the cross-sensitivity pattern and the concentration of the chemical or the combination of chemicals giving rise to the cross-sensitivity pattern; and removing the cross-sensitivity from the plurality of sensor outputs.

19. The method of claim 17, further comprising:
comparing the concentration of the chemical or combination of chemicals to a corresponding threshold for the chemical or combination of chemicals giving rise to the cross-sensitivity pattern, wherein the corresponding threshold for the chemical or combination of chemicals giving rise to the cross-sensitivity pattern is based at least in part on the determined current level of personal protective equipment associated with the individual; and providing an alert when the concentration of the chemical or combination of chemicals giving rise to the cross-sensitivity pattern exceeds the corresponding threshold.

20. The method of claim 16, further comprising:
determining, based on the cross-sensitivity pattern, a concentration of the chemical or combination of chemicals giving rise to the cross-sensitivity pattern;

receiving at least one measured value of the chemical or combination of chemicals giving rise to the cross-sensitivity pattern;

correlating the at least one measured value for the chemical or combination of chemicals giving rise to the cross-sensitivity pattern with the determined concentration of the chemical or combination of chemicals giving rise to the cross-sensitivity pattern; and updating the one or more known chemical patterns based on the correlating.

* * * * *